United States Patent

Grunenberg et al.

[11] Patent Number: 5,830,908
[45] Date of Patent: Nov. 3, 1998

[54] CRYSTALLINE HYDROCHLORIDE OF (R)-(-)-2-(N-[4-(1,1-DIOXIDO-3-OXO-2,3-DIHYDRO-BENZISOTHIAZOL-2-YL-)-BUTYL]-AMINOMETHYL)-CHROMAN

[75] Inventors: Alfons Grunenberg, Dormagen; Oliver Brehm, Wuppertal; Michael Conrad, Wuppertal; Dietrich Seidel, Wuppertal, all of Germany

[73] Assignee: Bayer Aktiengesellschaft, Leverkusen, Germany

[21] Appl. No.: 752,348

[22] Filed: Nov. 19, 1996

[30] Foreign Application Priority Data

Nov. 22, 1995 [DE] Germany ............ 195 43 478.1

[51] Int. Cl.⁶ ............ A61K 31/425; C07D 275/06
[52] U.S. Cl. ............ 514/373; 548/210
[58] Field of Search ............ 548/210; 514/373

[56] References Cited

U.S. PATENT DOCUMENTS

| | | | |
|---|---|---|---|
| 5,137,901 | 8/1992 | Junge et al. | 514/373 |
| 5,300,523 | 4/1994 | Junge et al. | 514/456 |
| 5,364,857 | 11/1994 | Bode-Greuel | 514/259 |
| 5,506,246 | 4/1996 | Junge et al. | 514/373 |
| 5,585,392 | 12/1996 | Junge et al. | 514/373 |

FOREIGN PATENT DOCUMENTS

| | | |
|---|---|---|
| 0 352 613 | 1/1990 | European Pat. Off. . |
| 352613 | 1/1990 | European Pat. Off. . |

*Primary Examiner*—Johann Richter
*Assistant Examiner*—Laura R. C. Lutz
*Attorney, Agent, or Firm*—Sprung Kramer Schaefer & Brisoe

[57] ABSTRACT

The invention relates to the crystalline form of the hydrochloride of the compound (R)-(-)-2-{N-[4-(1,1-dioxido-3-oxo-2,3-dihydro-benzisothiazol-2-yl)-butyl]-aminomethyl}-chroman, which is present as a stable form at room temperature. The crystalline modification V of the hydrochloride is suitable in particular for the preparation of solid medicaments, in particular of medicaments for the treatment of neuronal degenerations.

3 Claims, 6 Drawing Sheets

DSC-thermograms of DBCH

X-ray pattern of DBCH
Modification II.

Modification V.

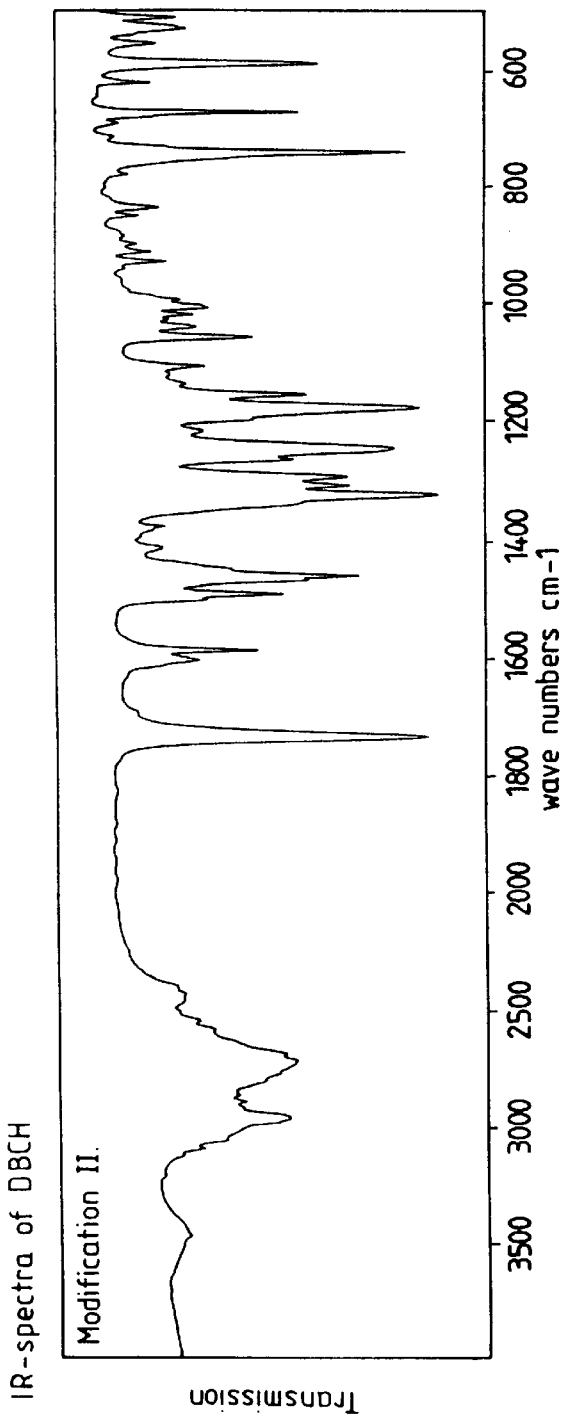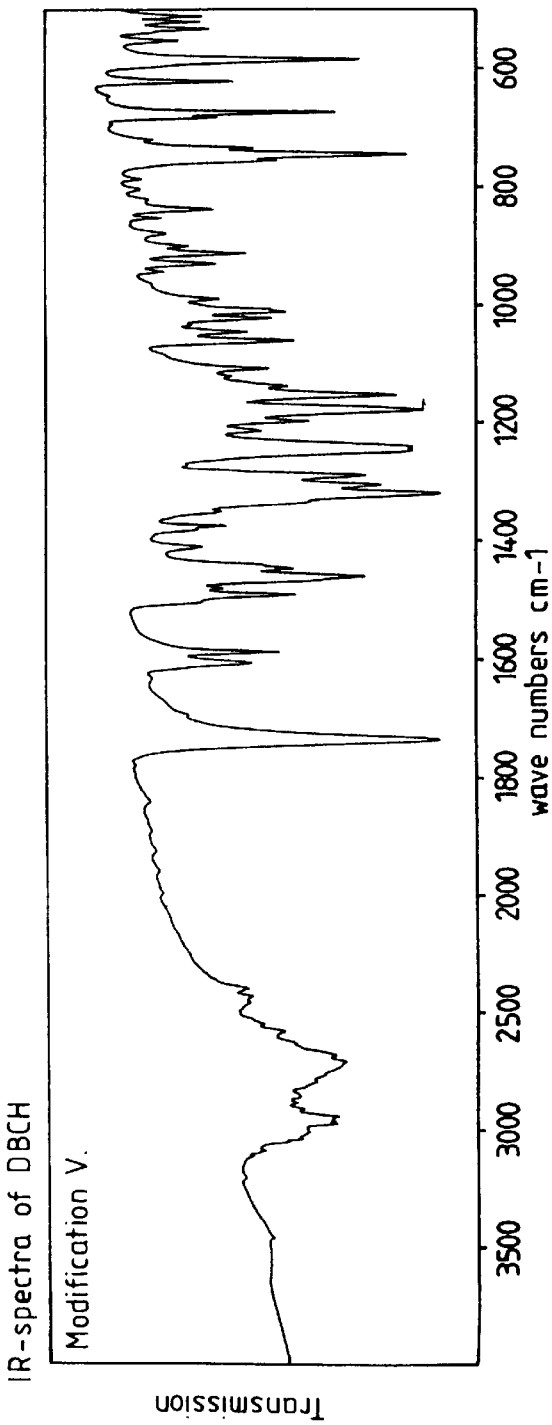

13C-solid state NMR spectra of DBCH
Modification II.

Modification V.

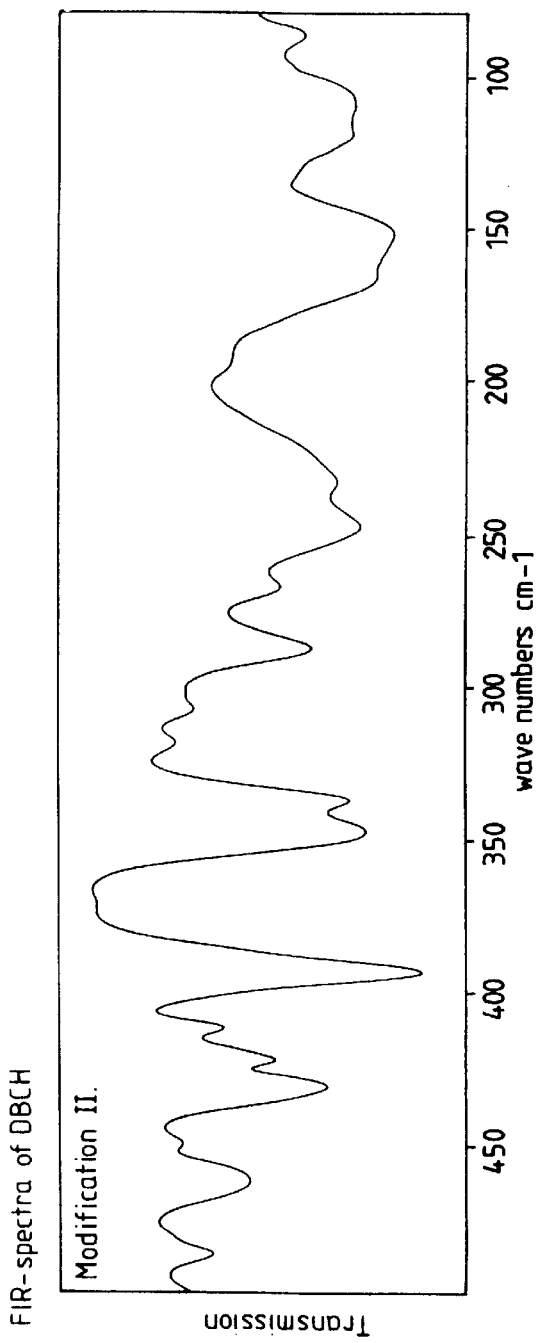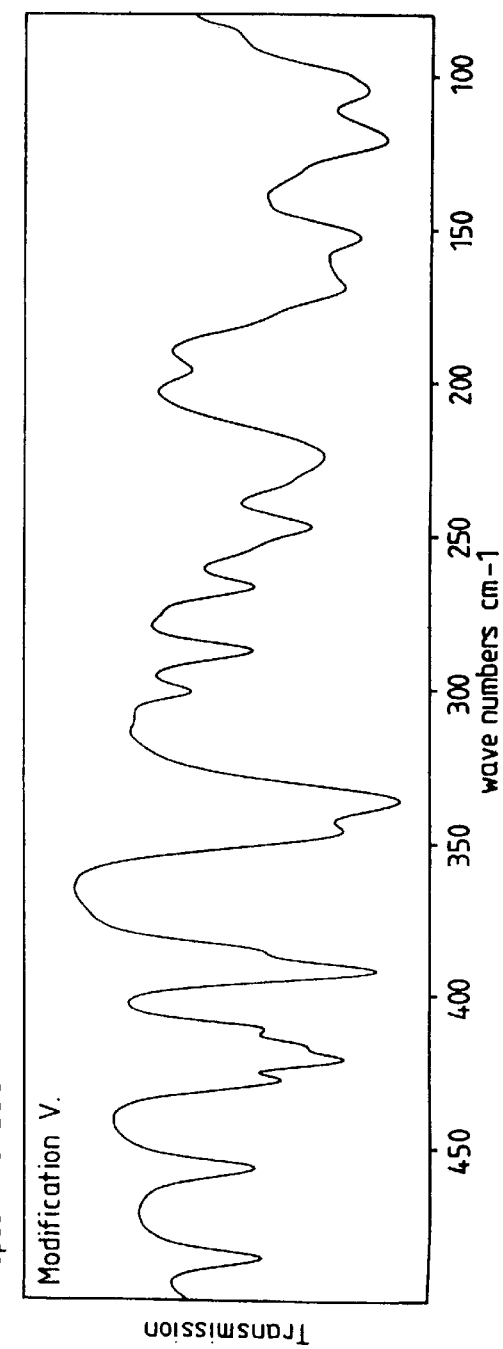

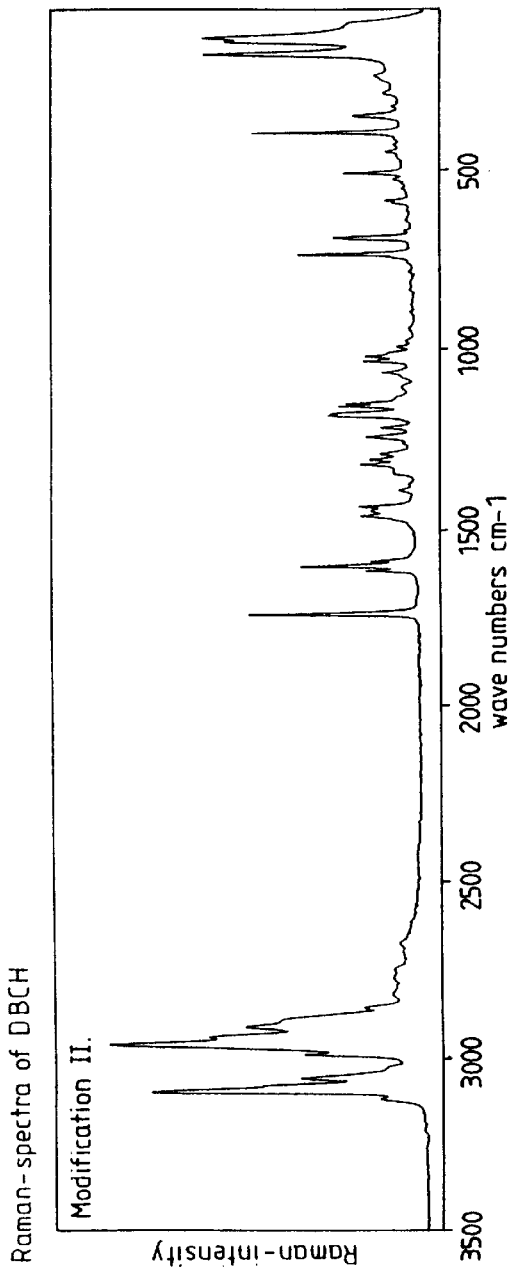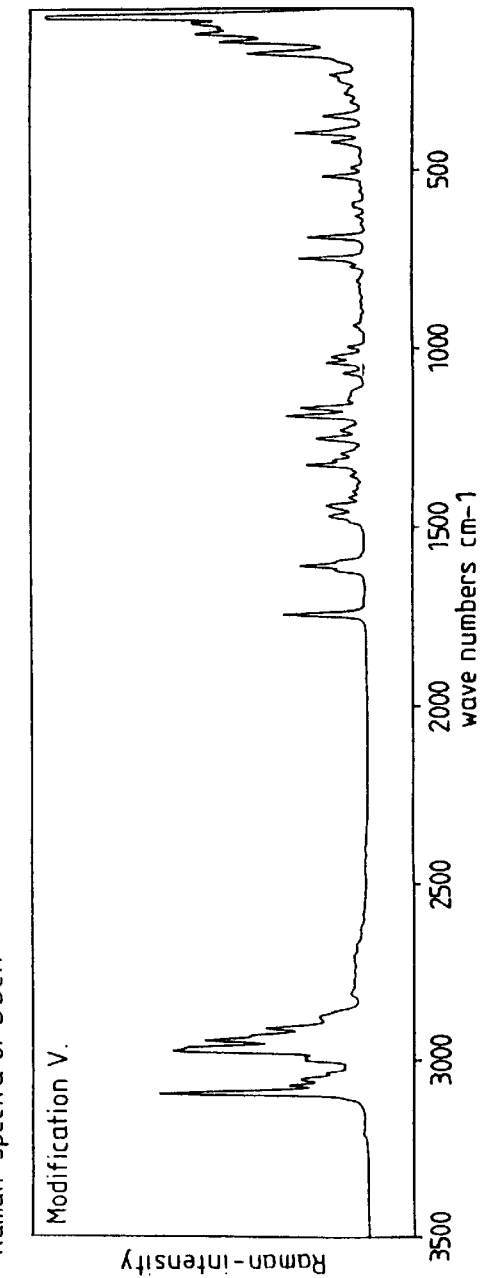

CRYSTALLINE HYDROCHLORIDE OF (R)-(-)-2-(N-[4-(1,1-DIOXIDO-3-OXO-2,3-DIHYDRO-BENZISOTHIAZOL-2-YL-)-BUTYL]-AMINOMETHYL)-CHROMAN

The invention relates to the crystalline form of the hydrochloride of the compound (R)-(-)-2-{N-[4-(1,1-dioxido-3-oxo-2,3-dihydro-benzisothiazol-2-yl)-butyl]-aminomethyl}-chroman, processes for the preparation and the use in medicaments, in particular in medicaments having a neuroprotective action.

The hydrochloride of the compound (R)-(-)-2-{N-[4-(1,1-dioxido-3-oxo-2,3-dihydro-benzisothiazol-2-yl)-butyl]-aminomethyl}-chroman has the formula (I)

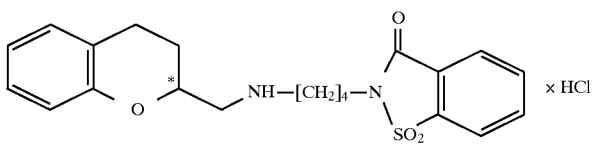

and is designated below as DBCH. The compound of the formula (I) is disclosed, for example, in European Patent Specification EP 352 613 as Example 92 H and, owing to its properties as a 5-$HT_{1A}$ agonist, is proposed, inter alia, as a neuroprotective active substance in medicaments, in particular for the treatment and prevention of neuronal degenerations due to ischaemic effects, such as a stroke.

In the patent specification mentioned, the preparation of DBCH is also described. It is carried out in general by reacting the optically active 2-aminomethylchroman with N-4-bromobutylsaccharin in an inert solvent in the presence of a base. In this way, the compound DBCH is obtained in a crystalline modification (referred to below as modification II). The melting point is stated as 192°–194° C.

It has been found that modification II is metastable and undergoes partial conversion at high humidity (85% relative humidity, room temperature). For this reason, it is only of limited suitability for use in pharmaceutical formulations.

Surprisingly, a crystalline form of the hydrochloride of (R)-(-)-2-{N-[4-(1,1-dioxido-3-oxo-2,3-dihydro-benzisothiazol-2-yl)-butyl]-aminomethyl}chroman (referred to below as modification V), which does not have these disadvantages, has now been found. This crystalline form of DBCH is thermodynamically stable and does not undergo conversion even at high atmospheric humidity (85% relative humidity, room temperature). For this reason, it is particularly suitable for solid medicament formulations.

BRIEF DESCRIPTION OF THE DRAWINGS

The crystalline form (modification V), according to the invention, of DBCH is defined by the following physico-chemical parameters.

1. The melting point of the crystalline form according to the invention cannot be determined experimentally since a solid-solid phase transition takes place on heating at about 60° C. to give modification I (endothermic peak in DSC thermogram, FIG. 1). The heat of transition is 24 J/g.

2. X-Ray diffraction pattern (cf.

| Mod. V [2 Theta] | Mod. V [2 Theta] | Mod. V [2 Theta] | Mod. V [2 Theta] |
|---|---|---|---|
| 9.7 | 22.5 | 28.4 | 35.1 |
| 11.5 | 22.6 | 27.7 | 35.3 |
| 12.3 | 23.2 | 29.2 | 35.7 |
| 12.6 | 24.0 | 29.3 | 36.2 |
| 13.4 | 24.4 | 29.8 | 36.4 |
| 14.5 | 24.7 | 30.1 | 36.7 |
| 15.7 | 24.9 | 31.1 | 37.0 |
| 16.8 | 25.8 | 31.8 | 37.4 |
| 16.9 | 26.0 | 32.6 | 37.6 |
| 17.5 | 26.3 | 33.9 | |
| 18.3 | 26.9 | 34.1 | |
| 19.4 | 27.4 | 34.3 | |
| 20.4 | 27.9 | 34.7 | |

3. IR spectrum (FIG. 3):

| Mod. V [$cm^{-1}$] | Mod. V [$cm^{-1}$] | Mod. V [$cm^{-1}$] | Mod. V [$cm^{-1}$] |
|---|---|---|---|
| 621 | 1010 | 1373 | 2847 |
| 672 | 1021 | 1408 | 2873 |
| 680 | 1044 | 1445 | 2899 |
| 716 | 1059 | 1458 | 2930 |
| 731 | 1106 | 1488 | 2949 |
| 743 | 1137 | 1585 | 2961 |
| 752 | 1153 | 1603 | 2993 |
| 783 | 1179 | 1690 | 3025 |
| 800 | 1197 | 1733 | 3073 |
| 835 | 1213 | 2389 | 3097 |
| 849 | 1242 | 2424 | 3189 |
| 876 | 1242 | 2448 | 3444 |
| 897 | 1248 | 2541 | |
| 910 | 1288 | 2571 | |
| 927 | 1305 | 2673 | |
| 940 | 1320 | 2701 | |
| 987 | 1348 | 2785 | |

Figure 1A:
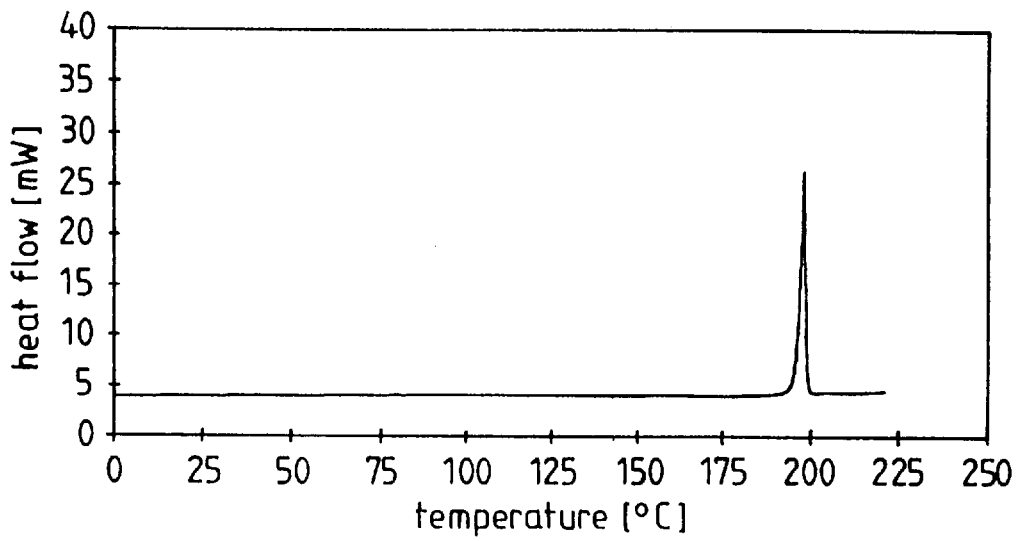
Figure 1B:
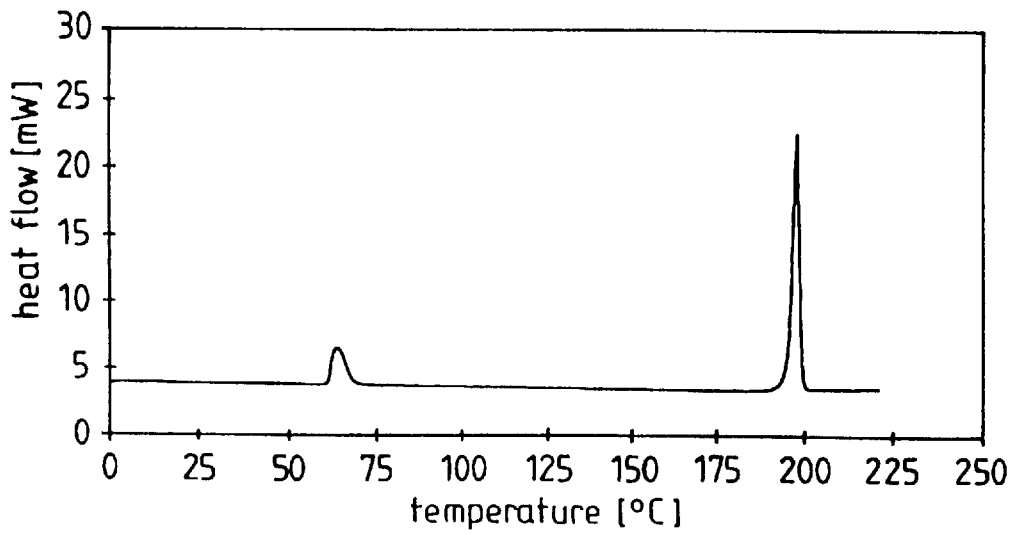
Figure 2A:
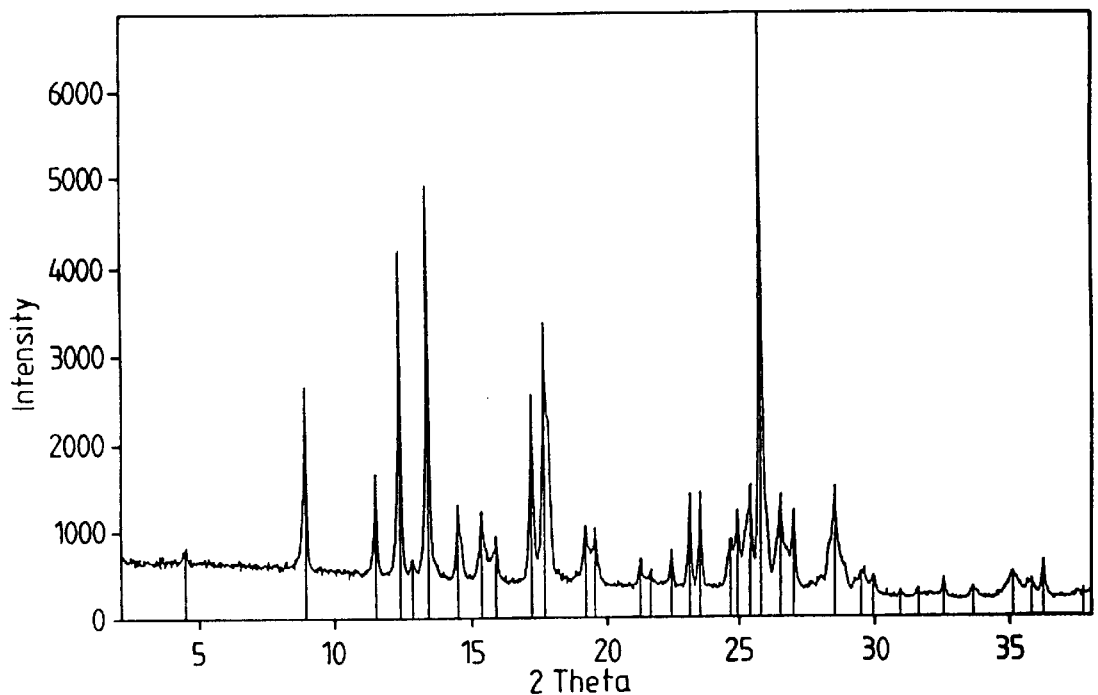
FIG. 2)
Figure 2B:
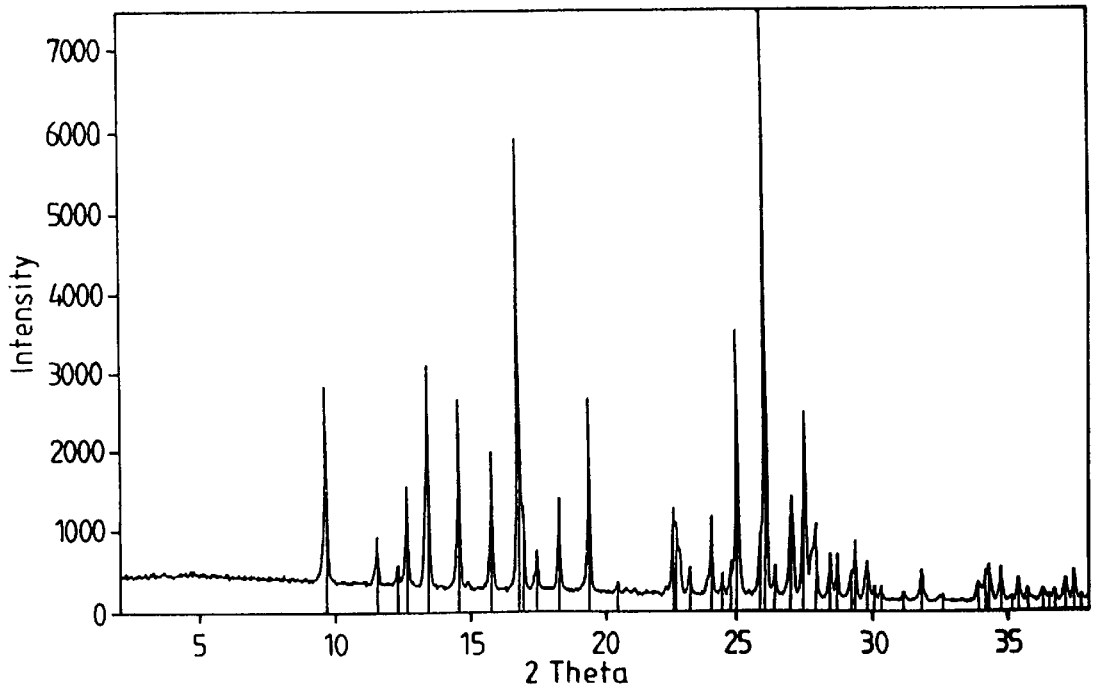
Figure 4A:
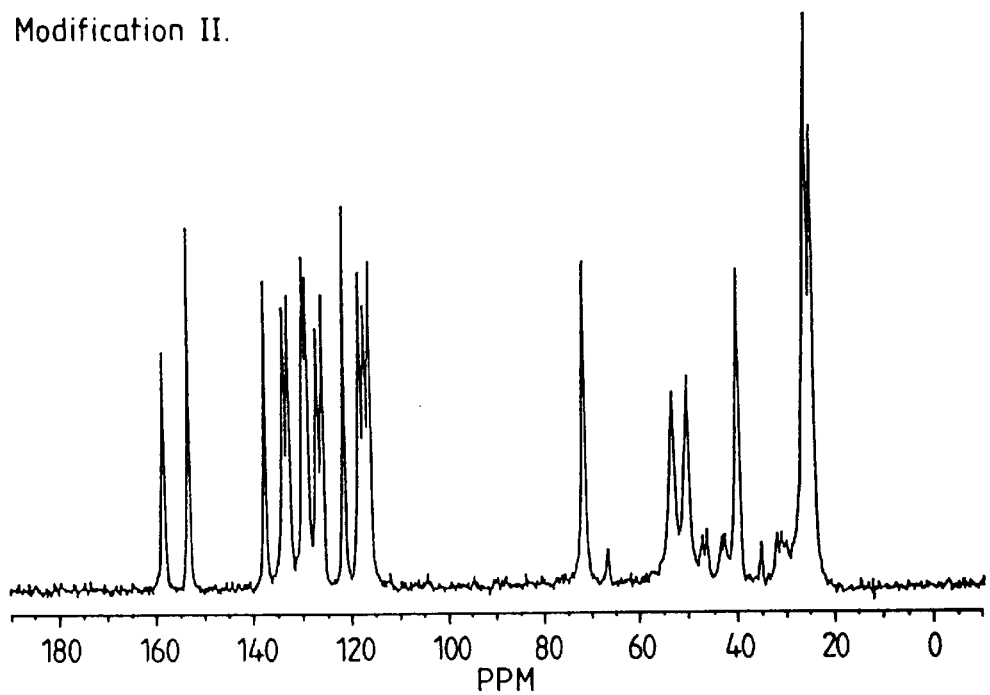
Figure 4B:
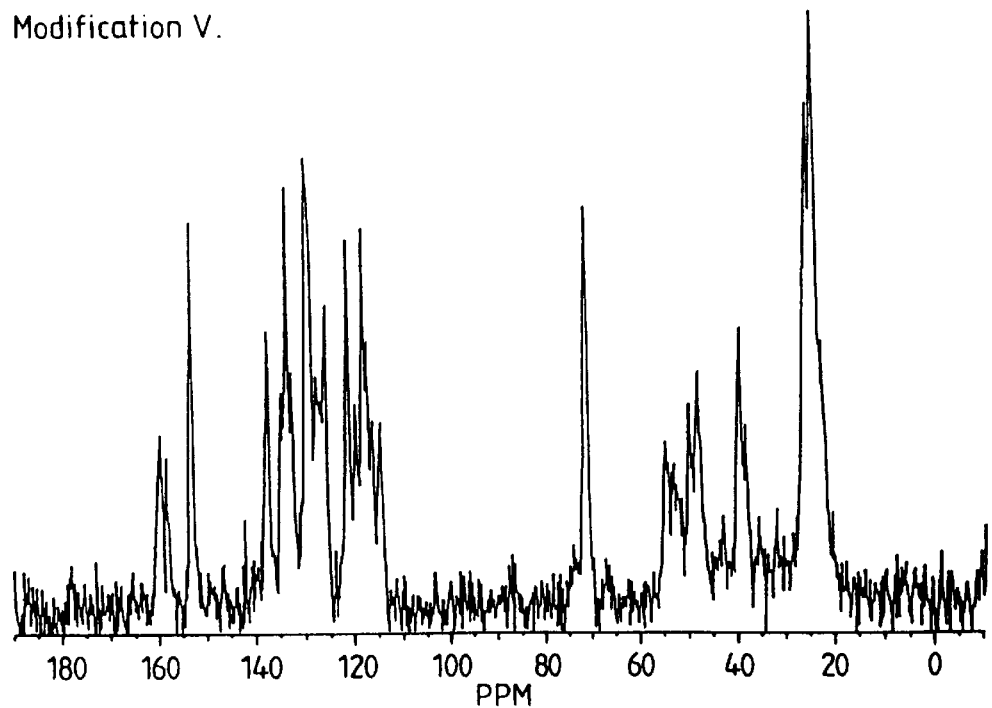

4. Solid-state $^{13}C$-NMR spectrum (FIG. 4)

| Mod. V [ppm] | Mod. V [ppm] | Mod. V [ppm] | Mod. V [ppm] |
|---|---|---|---|
| 159 | 128 | 72 | 26 |
| 158 | 126 | 55 | 25 |
| 153 | 121 | 54 | 23 |
| 137 | 120 | 50 | |
| 135 | 118 | 49 | |
| 134 | 117 | 40 | |
| 133 | 116 | 39 | |
| 130 | 115 | 27 | |

5. FIR spectrum (cf. FIG. 5)

| Mod. V [$cm^{-1}$] |
|---|
| 105 |
| 121 |
| 152 |
| 169 |
| 195 |
| 224 |
| 247 |
| 286 |
| 300 |
| 335 |
| 345 |
| 391 |
| 410 |
| 420 |
| 426 |

-continued

| Mod. V [cm$^{-1}$] |
|---|
| 455 |
| 485 |

6. Raman spectrum (cf. FIG. 6)

| Mod. V [cm$^{-1}$] | Mod. V [cm$^{-1}$] | Mod. V [cm$^{-1}$] | Mod. V [cm$^{-1}$] |
|---|---|---|---|
| 9 | 644 | 1379 | 3044 |
| 105 | 680 | 1394 | 3061 |
| 119 | 739 | 1411 | 3082 |
| 142 | 763 | 1433 | |
| 174 | 988 | 1462 | |
| 234 | 1016 | 1476 | |
| 286 | 1033 | 1600 | |
| 309 | 1062 | 1613 | |
| 348 | 1158 | 1736 | |
| 393 | 1181 | 2869 | |
| 419 | 1223 | 2900 | |
| 487 | 1245 | 2933 | |
| 513 | 1288 | 2963 | |
| 587 | 1307 | 2983 | |
| 595 | 1321 | 2991 | |
| 623 | 1351 | 3028 | |

The modification V differs substantially from the modification II in its physicochemical parameters DSC melting behaviour, X-ray diffraction pattern, IR spectrum, solid-state $^{13}$C-NMR spectrum, FIR spectrum and Raman spectrum (cf. FIGS. 1 to 6)). The melting point of the modification II is 195° C. (DSC, heating rate 10K/minute).

The preparation of the crystalline form according to the invention (modification V of DBCH) is carried out in general by suspending DBCH of modification II in water or inert organic substances, for example lower alcohols, ketones or alkanes, until the desired degree of transformation is reached, particularly preferably until quantitative transformation into modification V. As a rule, this transition takes place at temperatures of 0° C. to 35° C., preferably at 30° C. The resulting crystals of modification V are separated off and, in order to remove solvent present, are dried at room temperature in vacuo or at elevated temperature until the weight remains constant.

The crystalline modification V, according to the invention, of DBCH can be converted in a known manner into the customary formulations, formulations in which the crystalline active substance is present in solid form, such as, for example, tablets, sugar-coated tablets, pills, granular aerosols, suppositories and suspensions, being suitable. Here, the active substance is converted into the suitable formulation using inert nontoxic pharmaceutically suitable excipients and carriers.

EXPERIMENTAL PART

Preparation of seed crystals of modification V 0.5 g of DBCH of modification II is suspended in 8 ml of acetone:methanol (7:1) and stirred for 5 days at room temperature. The residue is filtered off and is dried at room temperature in vacuo until the weight remains constant. The IR spectrum is recorded in order to check for quantitative transformation.

Preparation of modification II

The active substance in the form of modification II is obtained in the synthesis of the active substance by the addition of about 1.5 mol equivalents of hydrochloric acid Modification II is precipitated from ethanol at about 5°–50° C., filtered off, then washed with ethanol and dried in vacuo at 95°–100° C.

EXAMPLES

Example 1

0.5 g of DBCH of modification II is suspended in 7 ml of acetone:ethanol (6:1). The suspension is seeded with the modification V and stirred for 5 days at 0° C. The residue is filtered off and is dried at room temperature in vacuo until the weight remains constant. The DSC thermogram is recorded in order to check for quantitative transition.

Example 2

0.5 g of DBCH of modification II is suspended in 6 ml of acetone:ethanol (2:1). The suspension is seeded with the modification V and stirred for 5 days at room temperature. The residue is filtered off and is dried at room temperature in vacuo until the weight remains constant. The IR spectrum is recorded in order to check for quantitative transition.

Example 3

1.7 g of DBCH of modification II are suspended in 14 ml of acetone:ethanol (6:1). The suspension is seeded with the modification V and stirred for 6 days at room temperature. The residue is filtered off and is dried at room temperature in vacuo until the weight remains constant. The X-ray diffraction pattern is recorded in order to check for quantitative transition.

Example 4

0.4 g of DBCH of modification II is suspended in 7 ml of acetone:ethanol (6:1). The suspension is seeded with the modification V and stirred for one week at 30° C. The residue is filtered off and is dried at room temperature in vacuo until the weight remains constant. The DSC thermogram is recorded in order to check for quantitative transformation.

Example 5

0.5 g of DBCH of modification II is suspended in 10 ml of iso-propanol. The suspension is seeded with the modification V and stirred for 6 h at room temperature. The residue is filtered off and is dried at room temperature in vacuo until the weight remains constant. The DSC thermogram is recorded in order to check for quantitative transition.

We claim:

1. Crystalline modification V of (R)-(-)-2-{N-[4-(1,1-dioxido-3-oxo-2,3-dihydro-benzisothiazol-2-yl)-butyl]-aminomethyl}-chroman hydrochloride.

2. A composition for the treatment and prevention of neuronal degenerations due to issemic events comprising an amount effective therefore according to claim 1 and a pharmacologically acceptable diluent.

3. The method for treating and preventing neuronal degenerations due to issemic events in a patient in need thereof which comprises administering such patient an amount effective therefore of the compound according to claim 1.

* * * * *

UNITED STATES PATENT AND TRADEMARK OFFICE
CERTIFICATE OF CORRECTION

PATENT NO. : 5,830,908
DATED : November 3, 1998
INVENTOR(S) : Grunenberg, et al.

It is certified that error appears in the above-identified patent and that said Letters Patent is hereby corrected as shown below:

Column 1, line 28, delete "ischaemic" and substitute --ischemic--.

Col. 4, line 57    Delete " issemic " and substitute -- ischemic --

Col. 4, line 61    Delete " issemic " and substitute -- ischemic --

Signed and Sealed this

Thirtieth Day of March, 1999

Attest:

Q. TODD DICKINSON

Attesting Officer    Acting Commissioner of Patents and Trademarks